(12) United States Patent
Cadieux et al.

(10) Patent No.: US 8,161,810 B2
(45) Date of Patent: Apr. 24, 2012

(54) SYRINGE IMAGING SYSTEMS

(75) Inventors: Ian Cadieux, San Diego, CA (US); Matthew Gerald Morris, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 1122 days.

(21) Appl. No.: 12/021,786

(22) Filed: Jan. 29, 2008

(65) Prior Publication Data

US 2009/0188311 A1    Jul. 30, 2009

(51) Int. Cl.
*G01F 17/00* (2006.01)
(52) U.S. Cl. ............................................ 73/149; 73/1.73
(58) Field of Classification Search ................... 73/149, 73/1.73; 382/106, 307
See application file for complete search history.

(56) References Cited

U.S. PATENT DOCUMENTS

| | | | |
|---|---|---|---|
| 4,838,857 A | 6/1989 | Strowe et al. | |
| 5,237,309 A | 8/1993 | Frantz et al. | |
| 5,425,716 A | 6/1995 | Kawasaki et al. | |
| 5,615,007 A | 3/1997 | Matsuura et al. | |
| 5,651,775 A * | 7/1997 | Walker et al. | 604/207 |
| 5,747,350 A * | 5/1998 | Sattler | 436/180 |
| 5,928,197 A | 7/1999 | Niehoff | |
| 6,500,151 B1 | 12/2002 | Cobb et al. | |
| RE38,189 E | 7/2003 | Walker et al. | |
| 7,169,135 B2 * | 1/2007 | Duchon et al. | 604/246 |
| 2003/0233069 A1 | 12/2003 | Gillespie, Jr. et al. | |
| 2004/0024361 A1 * | 2/2004 | Fago et al. | 604/152 |
| 2005/0217476 A1 | 10/2005 | Liang | |
| 2006/0129104 A1 * | 6/2006 | Cowan et al. | 604/181 |
| 2006/0144942 A1 | 7/2006 | Evans et al. | |
| 2006/0167414 A1 | 7/2006 | Scott et al. | |
| 2006/0178578 A1 | 8/2006 | Tribble et al. | |

FOREIGN PATENT DOCUMENTS

| | | |
|---|---|---|
| EP | 1049258 A2 | 11/2000 |
| EP | 1 279 410 A1 | 1/2003 |
| EP | 1433456 A1 | 6/2004 |
| WO | WO 96/25963 | 8/1996 |
| WO | WO 2005/004952 A1 | 1/2005 |

OTHER PUBLICATIONS

PCT International Search Report/Written Opinion for International Application No. PCT/US2009/032453, mailed May 4, 2009.

* cited by examiner

*Primary Examiner* — Frantz Jean
(74) *Attorney, Agent, or Firm* — McDermott Will & Emery LLP

(57) ABSTRACT

A syringe imaging system for a syringe infusion pump is provided. The system comprises an imaging device configured to capture one or more images of a syringe, and a processor, which is configured to determine, based on the one or more captured images, an internal diameter of the syringe and a distance between a bung and a bottom of the syringe, and to calculate a remaining volume of the syringe based upon the determined internal diameter and distance. A syringe infusion pump is also provided. The pump comprises a housing having a bracket configured to receive a syringe, a syringe driver configured to actuate a plunger of the syringe, an imaging device configured to capture one or more images of the syringe, and a processor. The processor is configured to determine, based on the one or more captured images, an internal diameter of the syringe and a distance between a bung and a bottom of the syringe, and to calculate a remaining volume of the syringe based upon the determined internal diameter and distance.

24 Claims, 5 Drawing Sheets

SYRINGE IMAGING SYSTEMS

CROSS-REFERENCE TO RELATED APPLICATION

Not applicable.

STATEMENT REGARDING FEDERALLY SPONSORED RESEARCH OR DEVELOPMENT

Not applicable.

FIELD

Embodiments of the present invention generally relate to medical devices and, in particular, relate to syringe imaging systems.

BACKGROUND

Syringe infusion pumps are often used to provide precise dosages of drugs injected for medical treatment via disposable syringes. They are especially effective for long-term injection of small volumes of solution where great accuracy is required, as the solution can be accurately delivered by precisely driving the plunger of a syringe down the syringe barrel at a continuous rate.

To achieve accurate flow rates and to determine the available and remaining volume of syringe, it is desirable to know the internal diameter of the syringe. In many syringe infusion pumps, user intervention is required to provide this information to the pump. For example, in some systems, the outside diameter of a syringe is measured with a linear potentiometer, and the system presents the user with a list of predetermined syringes known to have that outside diameter. The user then must either select or at least confirm the syringe type provided. Because the parameters of each syringe must be preprogrammed into the pump system, only a limited number of syringes are compatible with such a system.

Similarly, it is desirable to know the remaining distance a syringe plunger has to travel before the bung of the syringe meets the bottom of the syringe barrel. Some methods for determining the remaining plunger travel of a syringe have employed linear potentiometers to sense the position of the syringe plunger, based upon a user-selected hard-height for the particular syringe. These approaches are subject to error either from incorrectly selected syringes or from syringe variation (e.g., due to unacceptably large manufacturing tolerances). Still other approaches may measure the amount of force necessary to depress the plunger, and determine the syringe to be empty when the force exceeds a predetermined threshold. If the flow rate is low, however, such a system may result in long periods of non-delivery before the system determines the syringe to be empty.

SUMMARY

Embodiments described herein address the foregoing problems by providing a syringe imaging system that can automatically detect the internal diameter of a syringe, as well as the distance between the bung and the syringe barrel bottom. Based on this information, the syringe imaging system can calculate the remaining volume of the syringe. Accordingly, a syringe infusion pump utilizing such an imaging system is not limited to a predetermined list of compatible syringes, but can rather utilize any syringe physically compatible with the pump system. Moreover, by removing the need for operator input to determine the type of syringe provided, the safety and accuracy of the system is greatly improved.

Certain embodiments provide a syringe imaging system for a syringe infusion pump. The system comprises an imaging device configured to capture one or more images of a syringe in the syringe infusion pump, and a processor. The processor is configured to determine, based on the one or more captured images from the imaging device, an internal diameter of the syringe and a distance between a bung and a bottom of the syringe, and to calculate a remaining volume of the syringe based upon the determined internal diameter and distance.

Certain embodiments provide a syringe imaging system for a syringe infusion pump. The system comprises an imaging device configured to capture an image of a syringe, and a processor. The processor is configured to detect, in the captured image, a first internal wall of the syringe and a second internal wall of the syringe with an edge-detection algorithm, and to measure a distance between the first internal wall and the second internal wall to determine an internal diameter of the syringe.

Certain embodiments provide a syringe infusion pump comprising a housing having a bracket configured to receive a syringe, a syringe driver configured to actuate a plunger of the syringe, an imaging device configured to capture one or more images of the syringe, and a processor. The processor is configured to determine, based on the one or more captured images from the imaging device, an internal diameter of the syringe and a distance between a bung and a bottom of the syringe, and to calculate a remaining volume of the syringe based upon the determined internal diameter and distance.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

According to certain embodiments, a syringe imaging system provides a number of benefits in the administration of medication by a syringe infusion pump. For example, by automating syringe identification in an infusion pump, an accurate flow rate can be provided for any syringe which is physically compatible with the device. Moreover, removing user intervention from the syringe identification process can reduce the likelihood of misidentification and the resultant errors in medication dosage. Finally, by accurately tracking the remaining volume of medication in a syringe, the likelihood of an infusion pump attempting to continue to dispense medication from an exhausted syringe is also reduced.

Figure 1:
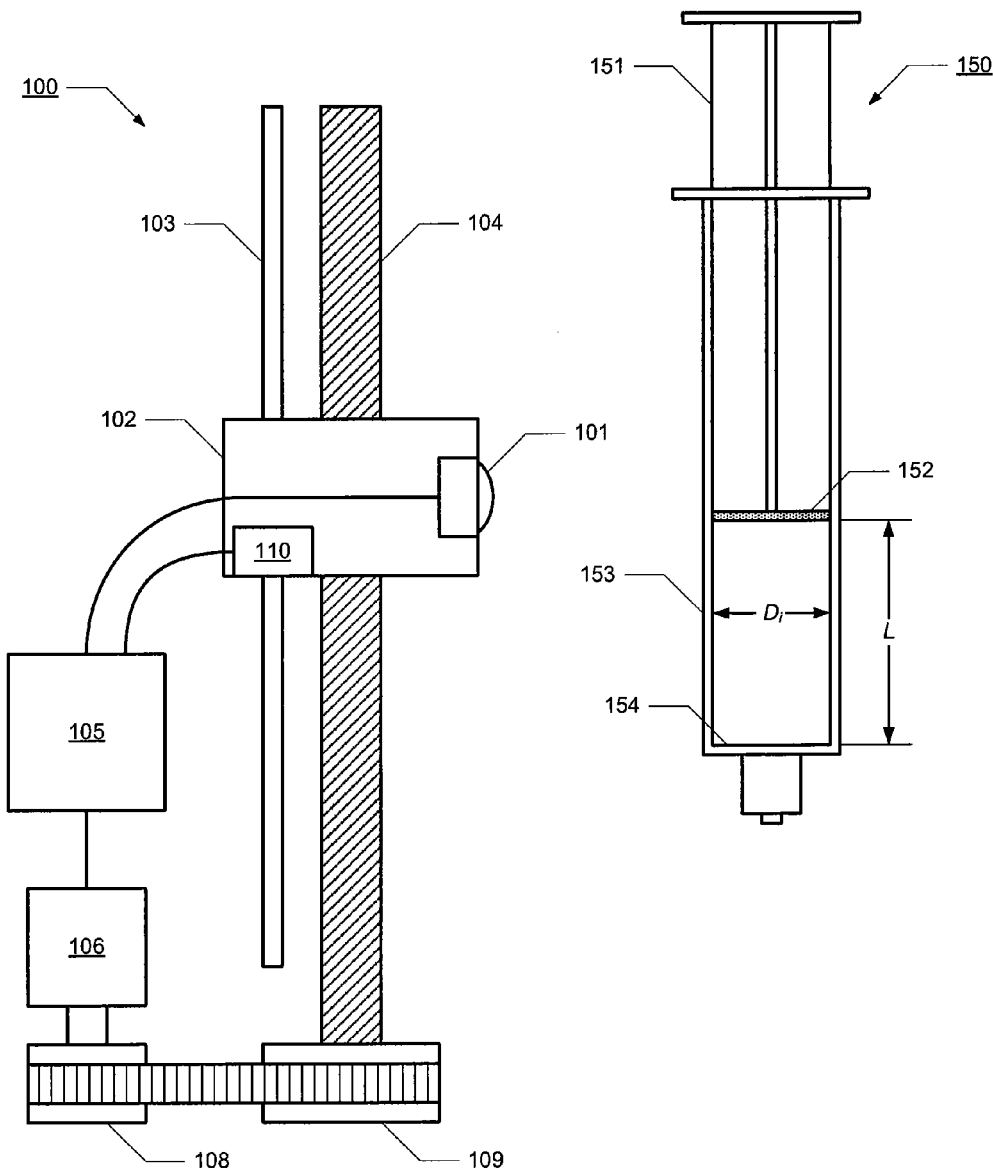
FIG. 1 is a block diagram illustrating a syringe imaging system in accordance with certain embodiments.

FIG. 1 is a block diagram illustrating syringe imaging system 100 in accordance with certain embodiments. Syringe imaging system 100 includes an imaging device 101 for capturing images of a syringe 150. The captured images are provided to a processor 105, which evaluates the image to determine the internal diameter $D_i$ of syringe 150 and the distance L between the bung 152 on the plunger 151 and the bottom 154 of the barrel 153 of syringe 150. The term "bung," as used herein, may refer either to a gasket provided at the bottom of a plunger of a syringe, or alternatively, to the bottom surface of the plunger (e.g., where there is no gasket provided).

In certain embodiments, imaging device 101 may be mounted on a motor-driven carriage 102, which carries imaging device 101 in a path parallel to syringe 150 along a guide rail 103 when driven by lead screw 104. This facilitates capturing multiple images of syringe 150 with imaging device 101 in various positions. In this regard, a motor 106 operably coupled to processor 105 may be used to rotate lead screw 104 via one or more gears, such as gears 108 and 109.

To determine the internal diameter $D_i$ of barrel 153 of syringe 150, processor 105 may employ an edge detection algorithm. When a captured image of syringe 150 is provided to processor 105, the processor evaluates the image in a predetermined horizontal orientation to locate internal surfaces (e.g., opposite sides of a circular barrel) or "walls" of barrel 153, based upon detected sharp changes in the luminous intensity of the captured image along the horizontal orientation. As will be readily understood by those of skill in the art, edge detection algorithms may compute a derivative of this intensity change, and determine, based upon a predetermined threshold, whether the rate of change of intensity represents an internal wall of barrel 153.

According to one aspect, for imaging device 101 to capture images in which the internal surfaces of syringe 150 are detectable, barrel 153 of syringe 150 should be transparent or at least translucent in a wavelength that imaging device 101 is capable of recording. For example, syringes which are transparent to visible light can be easily imaged with a commercial, off-the-shelf ("COTS") charge-coupled device ("CCD") or a complementary metal oxide semiconductor ("CMOS") camera module. Other syringes, which are transparent or translucent in other wavelengths, may also be utilized with appropriate imaging devices (e.g., ultraviolet, infrared, etc.). As will be readily apparent to those of skill in the art, imaging device 101 may be configured to capture images of syringe 150 in any wavelength in the electromagnetic spectrum, and the scope of the present invention is not limited by the foregoing exemplary embodiments.

To determine the distance L between bung 152 and bottom 154 of barrel 153, several different approaches may be used, according to certain embodiments. For example, if syringe 150 is sufficiently small, or if imaging device 101 can capture a sufficiently large field of view, a single captured image may be processed by processor 105, in a similar manner to that described above, to determine the location of bung 152 and bottom 154 using an edge detection algorithm. For larger syringes, however, it may be preferable to move imaging device 101 (via motor-driven carriage 102) along the length of syringe 150, capturing multiple images along the way. In this approach, as motor-driven carriage 102 moves along guide rail 103, imaging syringe 150, processor 105 is provided with information about the position of motor-driven carriage 102 by linear potentiometer 110. Accordingly, a captured image of bung 152 may be associated with a first linear position on guide rail 103, while a captured image of bottom 154 may be associated with a second linear position on guide rail 103, such that processor 105 can determine, based upon the distance traveled by motor-driven carriage (as determined by linear potentiometer 110), the distance L between bung 152 and bottom 154.

While the foregoing exemplary embodiment has been described with reference to a linear potentiometer for determining a linear position of motor-driven carriage 102 with respect to syringe 150, the scope of the present invention is not limited to such an arrangement. Rather, any one of a number of devices for sensing linear displacement may be used to provide information about the position of imaging device 101 to processor 105. For example, a rotary encoder may be used in conjunction with one of motor 106 or gears 108 and 109 to determine a position of motor-driven carriage 102 based upon a known pitch of lead screw 103. Other similar devices will be readily apparent to those of skill in the art, and are, for the sake of brevity, not recited herein.

Figure 2:
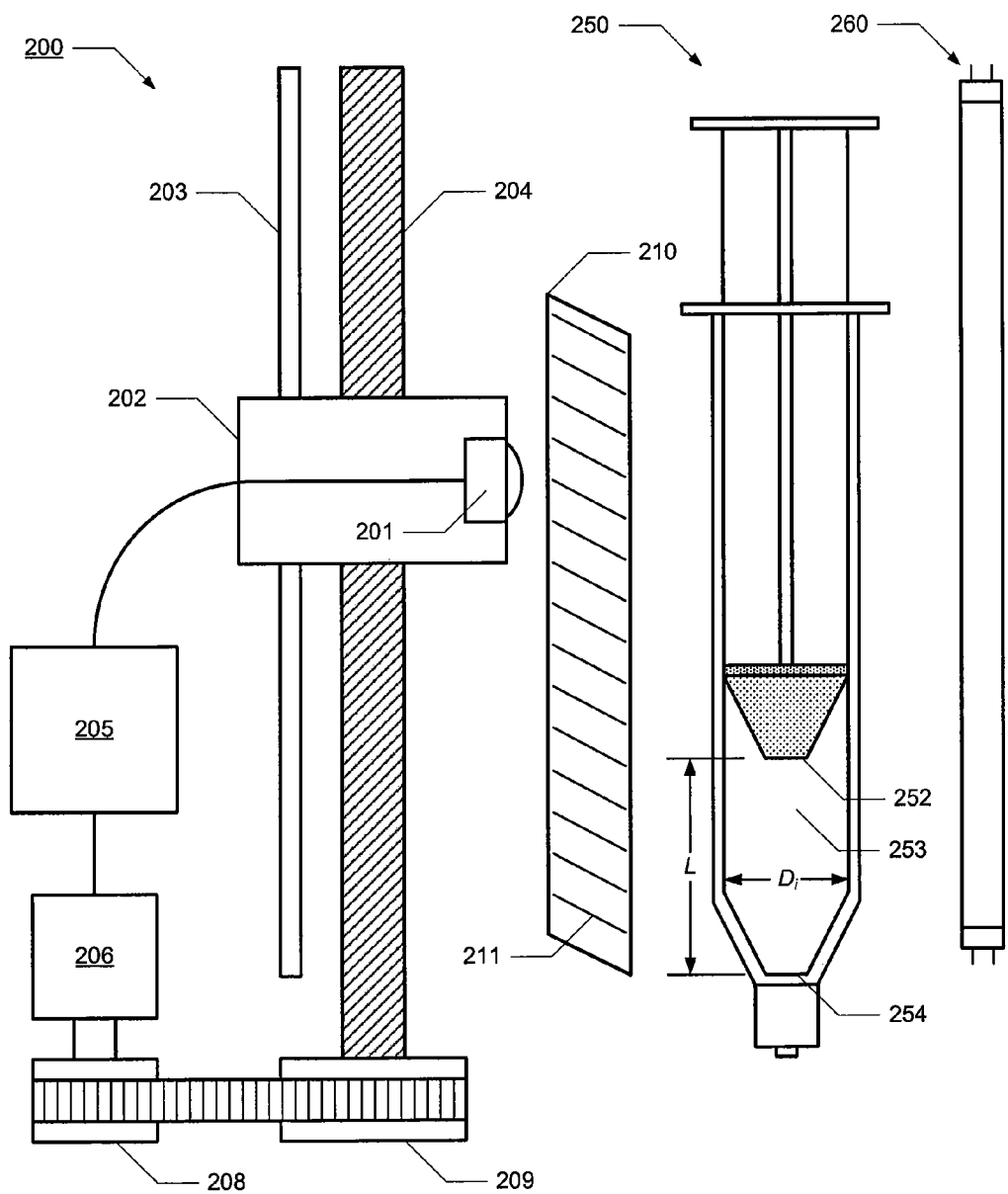
FIG. 2 is a block diagram illustrating a syringe imaging system in accordance with certain embodiments.

By way of further example, FIG. 2 illustrates a syringe imaging system 200 in accordance with certain embodiments, in which a graduated window 210 is used to determine the position of an imaging device 201 with respect to a syringe 250. Like the system illustrated in FIG. 1, syringe imaging system 200 includes imaging device 201 for capturing images of syringe 250. The captured images are provided to a processor 205, which evaluates the image to determine the internal diameter $D_i$ of syringe 150 and the distance L between the bung and the bottom of syringe 250. Imaging device 201 is mounted on a motor-driven carriage 202, which carries imaging device 201 in a path parallel to syringe 250 along a guide rail 203 when driven by lead screw 204. In this regard, a motor 206 operably coupled to processor 205 is used to rotate lead screw 204 via gears 208 and 209.

Rather than utilizing a linear potentiometer, rotary encoder, or other similar device to determine the position of motor-driven carriage 202 mechanically, however, syringe imaging system 200 includes graduated window 210, through which imaging device 201 views syringe 250. Graduated window 210 includes a number of graduations 211, which are visible in the images captured by imaging device 201. Graduations 211 may be, for example, etchings in window 210, or markings upon a surface of window 210. Processor 205 is configured to detect graduations 211 in the captured images, and to determine therefrom the vertical position of motor-driven carriage 202 and imaging device 201. With this information, processor 205 can determine the distance L between the bung 252 and the bottom 254 of the barrel 253 of syringe 250.

According to certain embodiments, to facilitate the imaging of a syringe such as syringe 250, a light source 260 may be provided opposite syringe 250 from imaging device 201. Light source 260 may provide illumination at a wavelength in which syringe 250 is transparent or at least translucent (e.g., not opaque), and in which imaging device 201 is capable of capturing images.

In accordance with certain aspects, a syringe need not be a simple cylinder for a syringe imaging system to calculate the remaining volume thereof. For example, syringe 250 has a barrel with a circular cross section, but a bung and a bottom with a partially conic shape. By calculating the distance between the bottom surface of bung 252 and bottom 254 of barrel 253, processor 205 can calculate the remaining volume V of syringe 250 with the formula $V=\pi D_i \times L$, as the volume "missing" from the bottom of barrel 253 (compared with a cylindrical barrel) is made up by the extra volume of solution surrounding bung 252 (i.e., the solution present in barrel 253 above the bottom surface of bung 252).

While the foregoing exemplary embodiments have been described with reference to arrangements in which a single imaging device is mounted on a motor-driven carriage to image various portions of a syringe, the scope of the present invention is not limited to such an arrangement. Rather, any number of imaging devices may be used to capture images of a syringe. For example, a 2-D imaging array may be utilized, without a motor-driven carriage, to capture one or more images of a syringe from which a processor can determine both the internal diameter and remaining plunger travel of a syringe. Alternatively, a combination of several 2-D and/or linear arrays may be utilized, one oriented parallel to the barrel of the syringe to determine the remaining plunger travel thereof, and another oriented perpendicular to the barrel to determine the internal diameter thereof.

Figure 3:
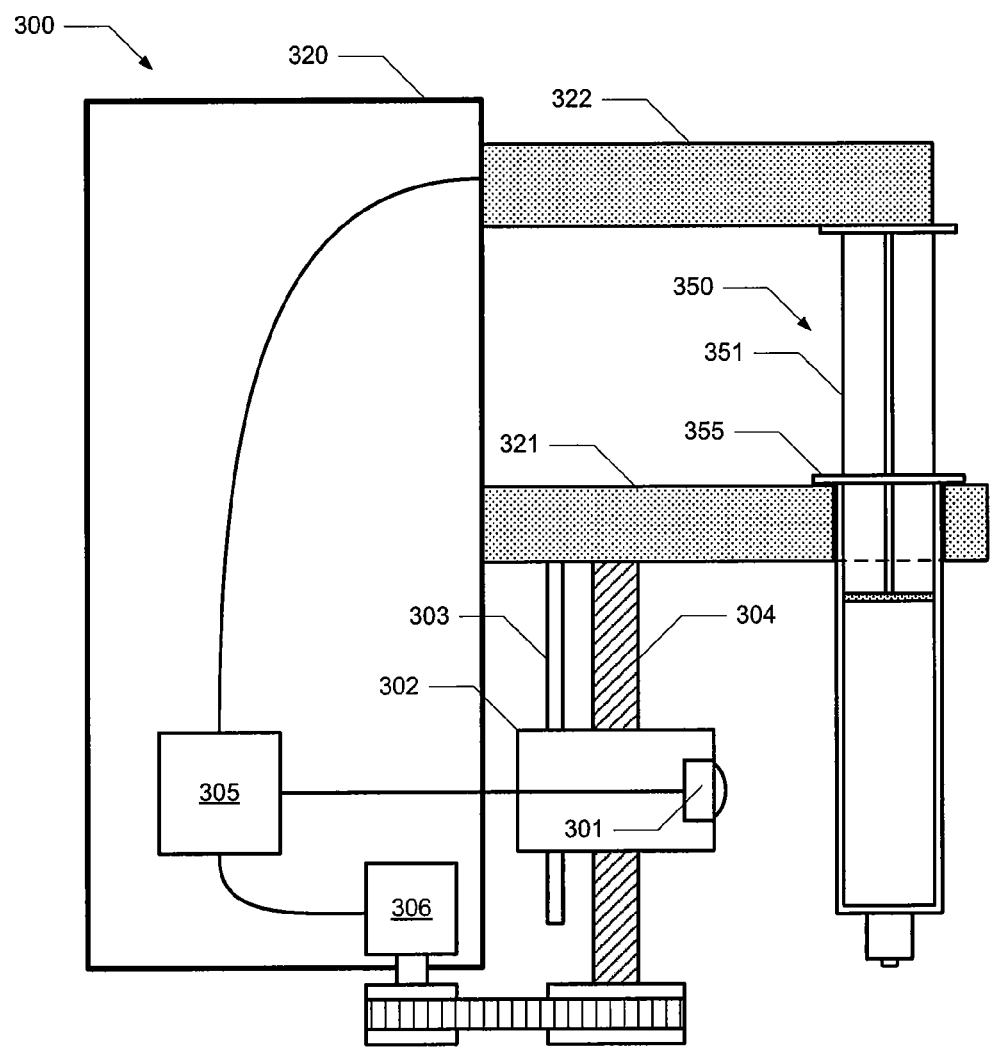
FIG. 3 is a block diagram illustrating a syringe infusion pump in accordance with certain embodiments.

Turning to FIG. 3, a block diagram of a syringe infusion pump 300 is illustrated in accordance with certain embodiments. Syringe infusion pump 300 includes a housing 320, on which is mounted a bracket 321. The bracket is configured to receive a syringe 350, and to retain syringe 350 by a flange 355 thereof. Syringe infusion pump 300 further includes a syringe driver 322 which is configured to actuate a plunger 351 of syringe 350 in response to commands from a processor 305.

Syringe infusion pump 300 further includes an imaging device 301 configured to capture one or more images of syringe 350. The captured images are provided to processor 305, which evaluates the images to determine the internal diameter and remaining plunger travel of syringe 350. Imaging device 301 is mounted on a motor-driven carriage 302, which carries imaging device 301 in a path parallel to syringe 350 along a guide rail 303 when driven by lead screw 304. This facilitates capturing multiple images of syringe 350 with imaging device 301 in various positions. For example, when a syringe such as syringe 350 is first loaded into syringe infusion pump 300, motor-driven carriage 302 travels along guide rail 303 parallel to syringe 350, carrying imaging device 301 and allowing imaging device 301 to take several images of the length of syringe 350. As set forth above, these images are used by processor 305 to determine the internal diameter and remaining plunger travel of syringe 350.

Motor 306 may be used to rotate lead screw 304 via one or more gears to move motor-driven carriage 302 along guide rail 303. In an alternative embodiment, motor 306 may be directly coupled to lead screw 304, bypassing the need for gears. In certain embodiments, motor 306 may also be configured to actuate syringe driver 322. In other embodiments, a separate motor may be used for actuating syringe driver 322.

While the foregoing exemplary embodiments have been described with reference to a motor-driven carriage being translated along the length of a syringe by a lead screw, the scope of the present invention is not limited to such an arrangement. Rather, as will be apparent to those of skill in the art, a motor-driven carriage may be moved by any one of a number of devices, including, for example, a drive belt, a drive chain, a rack-and-pinion gear arrangement, etc.

Figure 4:
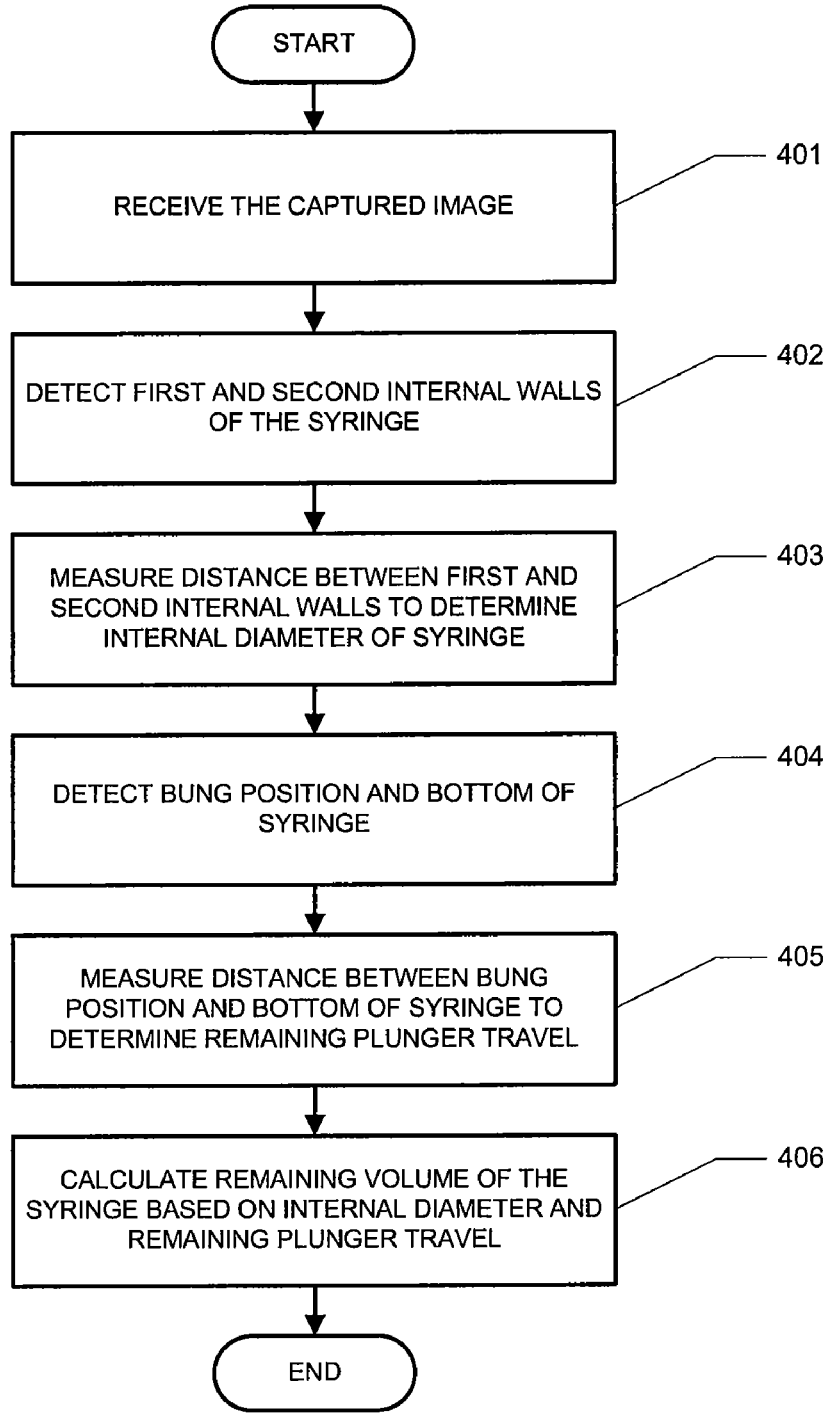
FIG. 4 is a flowchart illustrating a method for determining the remaining volume of a syringe in accordance with certain embodiments.

To determine the internal diameter $D_i$ and remaining plunger travel L of syringe 350, processor 305 may employ an edge detection algorithm. For example, FIG. 4 is a flowchart illustrating a method of determining the remaining volume of a syringe, according to certain embodiments. The method begins with step 401, in which the image captured by imaging device 301 is provided to processor 305. In step 402, processor 305 evaluates the image in a predetermined horizontal orientation to locate internal surfaces (e.g., opposite sides of a circular barrel) or "walls" of syringe 350, using an edge detection algorithm. In step 403, processor 305 measures the distance between the walls located in step 402. According to certain embodiments, processor 305 may be pre-programmed with information regarding the focal distance of imaging device 301, such that the scale for the captured image is known, to assist in the determination of distance between the walls.

In step 404, processor 305 evaluates the image in a predetermined vertical orientation to locate the bung and the bottom of the barrel of syringe 350, using an edge detection algorithm. In step 405, processor 305 measures the distance between the bung and the bottom located in step 404. Based upon the distances measured in steps 403 and 405, processor 305 calculates the remaining volume of syringe 350 in step 406.

While the foregoing exemplary embodiment has been described with reference to the syringe infusion pump of FIG. 3, the scope of the present invention is not limited to this particular arrangement. Rather, in accordance with certain embodiments, a method of determining the remaining volume of a syringe has application to any number of different syringe imaging systems, such as, for example, the syringe imaging systems illustrated in FIGS. 1 and 2.

Figure 5:
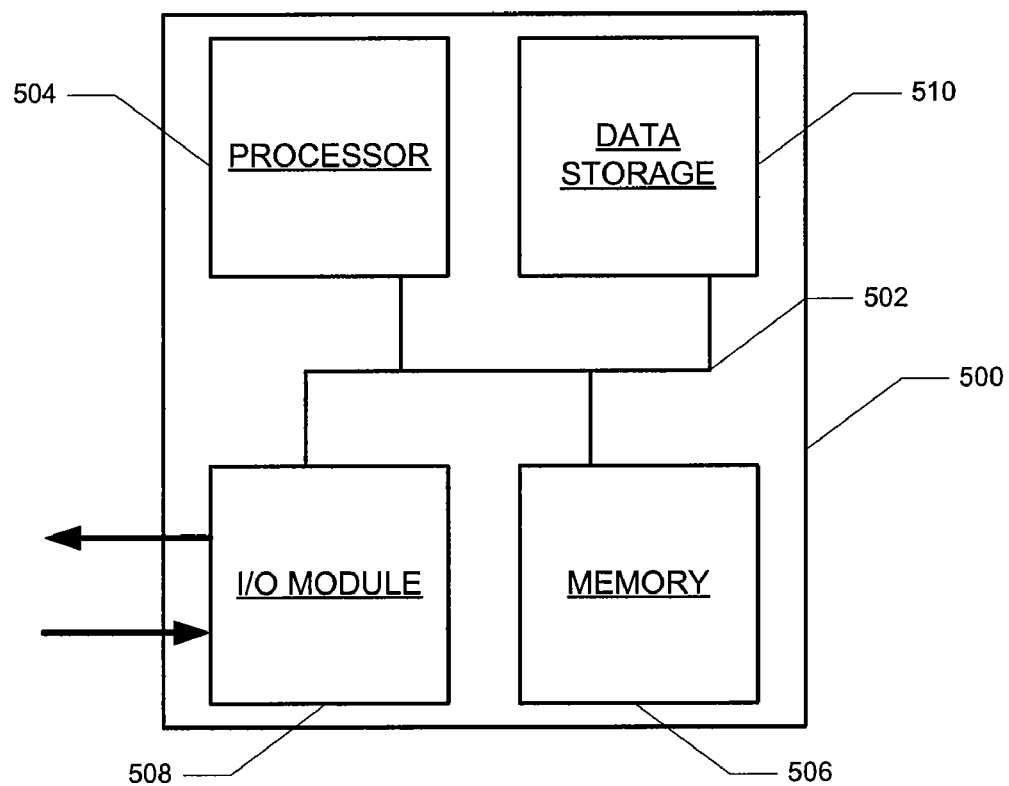
FIG. 5 is a block diagram that illustrates a computer system upon which certain embodiments may be implemented.

FIG. 5 is a block diagram that illustrates a computer system 500 upon which an embodiment may be implemented. Computer system 500 includes a bus 502 or other communication mechanism for communicating information, and a processor 504 coupled with bus 502 for processing information. Computer system 500 also includes a memory 506, such as a random access memory ("RAM") or other dynamic storage device, coupled to bus 502 for storing information and instructions to be executed by processor 504. Memory 506 may also be used for storing temporary variable or other intermediate information during execution of instructions to be executed by processor 504. Computer system 500 further includes a data storage device 510, such as a magnetic disk or optical disk, coupled to bus 502 for storing information and instructions.

Computer system 500 may be coupled via I/O module 508 to a display device (not illustrated), such as a cathode ray tube ("CRT") or liquid crystal display ("LCD") for displaying information to a computer user. An input device, such as, for example, a keyboard or a mouse may also be coupled to computer system 500 via I/O module 508 for communicating information and command selections to processor 504.

According to one embodiment, calculating the remaining volume of a syringe is performed by a computer system 500 in response to processor 504 executing one or more sequences of one or more instructions contained in memory 506. Such instructions may be read into memory 506 from another machine-readable medium, such as data storage device 510. Execution of the sequences of instructions contained in main memory 506 causes processor 504 to perform the process steps described herein. One or more processors in a multi-processing arrangement may also be employed to execute the sequences of instructions contained in memory 506. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 504 for execution. Such a medium may take many forms, including, but not limited to, non-volatile media, volatile media, and transmission media. Non-volatile media include, for example, optical or magnetic disks, such as data storage device 510. Volatile media include dynamic memory, such as memory 506. Transmission media include coaxial cables, copper wire, and fiber optics, including the wires that comprise bus 502. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the sprit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the invention, and are not referred to in connection with the interpretation of the description of the invention. All structural and functional equivalents to the elements of the various embodiments described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A syringe imaging system for a syringe infusion pump, comprising:
    an imaging device configured to capture one or more images of a syringe in the syringe infusion pump; and
    a processor configured to:
        determine, based on the one or more captured images from the imaging device, an internal diameter of the syringe and a distance between a bung and a bottom of the syringe, and
        calculate a remaining volume of the syringe based upon the determined internal diameter and distance.

2. The syringe imaging system of claim 1, further comprising a motor-driven carriage coupled to the imaging device, wherein the motor-driven carriage is configured to carry the imaging device along a path parallel to the syringe.

3. The syringe imaging system of claim 2, wherein the motor-driven carriage is operably coupled to a motor via one or more of: a lead screw, a drive belt, a drive chain and one or more gears.

4. The syringe imaging system of claim 2, wherein the motor-driven carriage includes a position sensing device, whereby a linear position of the motor-driven carriage in relation to the syringe is determined.

5. The syringe imaging system of claim 4, wherein the position sensing device is either a linear potentiometer or a rotary encoder.

6. The syringe imaging system of claim 2, further comprising a window with gradation marks through which the imaging device captures the one or more images of the syringe, whereby a linear position of the motor-driven carriage in relation to the syringe is determined.

7. The syringe imaging system of claim 1, further comprising a light source located such that the syringe is between the light source and the imaging device.

8. The syringe imaging system of claim 7, wherein the light source emits a light in a wavelength in which the syringe is at least partially transparent.

9. The syringe imaging system of claim 1, wherein the imaging device is selected from the group consisting of a CMOS camera module, a CCD camera module, a 2-D imaging array and a linear imaging array.

10. The syringe imaging system of claim 1, wherein the processor is configured to determine the internal diameter of the syringe edge by detecting a first internal wall of the syringe and a second internal wall of the syringe and measuring a distance between the first internal wall and the second internal wall.

11. The syringe imaging system of claim 10, wherein the processor is configured to detect the first and second internal walls with an edge-detection algorithm.

12. A syringe imaging system for a syringe infusion pump, the system comprising:
    an imaging device configured to capture an image of a syringe; and
    a processor configured to:
        detect, in the captured image, a first internal wall of the syringe and a second internal wall of the syringe;
        measure a distance between the first internal wall and the second internal wall to determine an internal diameter of the syringe;
        detect, in the captured image, the bung of the syringe and the bottom of the syringe with an edge-detection algorithm; and
        measure a distance between the bung and the bottom to determine a remaining plunger travel of the syringe.

13. The syringe imaging system of claim 12, wherein the processor is configured to detect the first and second internal walls with an edge-detection algorithm.

14. The syringe imaging system of claim 12, wherein the processor is further configured to determine a remaining volume of the syringe based upon the determined internal diameter and the determined plunger travel.

15. A syringe infusion pump comprising:
a housing having a bracket configured to receive a syringe;
a syringe driver configured to actuate a plunger of the syringe;
an imaging device configured to capture one or more images of the syringe; and
a processor configured to:
   determine, based on the one or more captured images from the imaging device, an internal diameter of the syringe and a distance between a bung and a bottom of the syringe, and
   calculate a remaining volume of the syringe based upon the determined internal diameter and distance.

16. The syringe infusion pump of claim 15, further comprising:
a motor-driven carriage coupled to the imaging device, wherein the motor-driven carriage is configured to carry the imaging device along a path parallel to the syringe.

17. The syringe infusion pump of claim 16, further comprising a motor configured to actuate the syringe driver and/or to power the motor-driven carriage.

18. The syringe infusion pump of claim 16, wherein the motor-driven carriage includes a position sensing device, whereby a linear position of the motor-driven carriage in relation to the syringe is determined.

19. The syringe infusion pump of claim 18, wherein the position sensing device is either a linear potentiometer or a rotary encoder.

20. The syringe infusion pump of claim 16, further comprising a window with gradation marks through which the imaging device captures the one or more images of the syringe, whereby a linear position of the motor-driven carriage in relation to the syringe is determined.

21. The syringe infusion pump of claim 15, further comprising a light source located such that the syringe is between the light source and the imaging device.

22. The syringe infusion pump of claim 15, wherein the imaging device is selected from the group consisting of a CMOS camera module, a CCD camera module, a 2-D imaging array and a linear imaging array.

23. The syringe infusion pump of claim 15, wherein the processor is configured to determine the internal diameter of the syringe edge by detecting, with an edge-detection algorithm, a first internal wall of the syringe and a second internal wall of the syringe, and by measuring a distance between the first internal wall and the second internal wall.

24. The syringe infusion pump of claim 15, wherein the processor is further configured to automatically determine the remaining volume of the syringe when the syringe is first provided in the syringe infusion pump.

* * * * *